US012678567B2

(12) United States Patent

Gyory et al.

(10) Patent No.: US 12,678,567 B2
(45) Date of Patent: Jul. 14, 2026

(54) SMART SYRINGE WITH DOSE CAPTURE AND APP FOR SMART PHONE

(71) Applicant: Becton, Dickinson and Company, Franklin Lakes, NJ (US)

(72) Inventors: J. Richard Gyory, Sudbury, MA (US); Carlos Morales, Tewksbury, MA (US); Bo Yang Yu, Winchester, MA (US); Eric Sun, Waltham, MA (US); Kai Qian, Wilmington, MA (US); Kepei Sun, Andover, MA (US); Dana Killam, Chester, NH (US); Alessandro Pizzochero, Chelmsford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 824 days.

(21) Appl. No.: 17/921,701

(22) PCT Filed: Apr. 26, 2021

(86) PCT No.: PCT/US2021/029054
§ 371 (c)(1),
(2) Date: Oct. 27, 2022

(87) PCT Pub. No.: WO2021/222054
PCT Pub. Date: Nov. 4, 2021

(65) Prior Publication Data
US 2023/0166044 A1    Jun. 1, 2023

Related U.S. Application Data

(60) Provisional application No. 63/017,347, filed on Apr. 29, 2020.

(51) Int. Cl.
*A61M 5/315*       (2006.01)
*A61M 5/20*        (2006.01)
*A61M 5/32*        (2006.01)

(52) U.S. Cl.
CPC ...... *A61M 5/31546* (2013.01); *A61M 5/2033* (2013.01); *A61M 5/3202* (2013.01);
(Continued)

(58) Field of Classification Search
None
See application file for complete search history.

(56) References Cited

U.S. PATENT DOCUMENTS 5,902,982 A       5/1999  Lappe
2009/0043253 A1*  2/2009  Podaima ................ G16H 10/60
                                                              604/67
(Continued)

FOREIGN PATENT DOCUMENTS

GB        701232 A       12/1953
JP        2008-142565 A   6/2008
(Continued)

OTHER PUBLICATIONS

International Search Report dated Aug. 10, 2021, which issued in the corresponding PCT Application No. PCT/US2021/029054.

*Primary Examiner* — Manuel A Mendez
(74) *Attorney, Agent, or Firm* — Dickinson Wright PLLC

(57)            ABSTRACT

A smart syringe system and method are provided. The system includes a smart syringe and an external device. The syringe obtains data of a dose administered to a patient and wirelessly transmit the data to the external device. Alternately, the external device obtains the data via an image of the syringe. The external device may execute an application configured to process the data and display information of the dose.

10 Claims, 11 Drawing Sheets

(52) U.S. Cl.
CPC ............... *A61M 2005/2013* (2013.01); *A61M 2205/3584* (2013.01); *A61M 2205/502* (2013.01); *A61M 2205/52* (2013.01)

(56) References Cited

U.S. PATENT DOCUMENTS

| | | | | |
|---|---|---|---|---|
| 2010/0286609 | A1* | 11/2010 | Mahurkar | A61M 5/502 |
| | | | | 604/110 |
| 2013/0345641 | A1 | 12/2013 | Cerman et al. | |
| 2015/0209114 | A1 | 7/2015 | Burkhole et al. | |
| 2016/0259913 | A1 | 9/2016 | Yu et al. | |
| 2017/0286638 | A1* | 10/2017 | Searle | G16H 40/63 |
| 2018/0261322 | A1 | 9/2018 | Cheng et al. | |
| 2018/0344941 | A1 | 12/2018 | Cowe | |
| 2019/0117888 | A1 | 4/2019 | Burkholz et al. | |
| 2019/0224406 | A1 | 7/2019 | Cowan et al. | |
| 2019/0341136 | A1 | 11/2019 | Hopper et al. | |

FOREIGN PATENT DOCUMENTS

| | | | |
|---|---|---|---|
| JP | 2013-533076 | A | 8/2013 |
| JP | 2013-189241 | A | 9/2013 |
| JP | 2017510880 | A | 4/2017 |
| JP | 2017-527414 | A | 9/2017 |
| JP | 2017-530772 | A | 10/2017 |
| JP | 2018-530814 | A | 10/2018 |
| JP | 2019505333 | A | 2/2019 |
| WO | 2005/097232 | A1 | 10/2005 |
| WO | 2014/133053 | A1 | 9/2014 |

* cited by examiner

<u>Related Art</u>

SMART SYRINGE WITH DOSE CAPTURE AND APP FOR SMART PHONE

CROSS-REFERENCE TO RELATED APPLICATION

This Application claims priority from U.S. Provisional Application 63/017,347 filed Apr. 29, 2020, in the United States Patent and Trademark Office, the disclosure of which is incorporated herein by reference in its entirety.

BACKGROUND

1. Field

Apparatuses and methods consistent with example embodiments relate to syringes for transferring (i.e., injecting or withdrawing) fluids, and more particularly to a smart syringe that senses and provides information, relating to fill volume and dose, and may transmit the information to a smart phone application (app).

2. Description of the Related Art

Medication non-adherence is an issue of global importance, particularly with regard to diabetes care. An estimated fifty percent of all patients do not take their medication as prescribed. Non-adherence directly contributes to hundreds of thousands of deaths and billions of dollars in avoidable medical and related costs.

Smartphone apps are currently in use, which use a picture of a prescription label to help a patient reorder when their supply of prescribed medication is low. However, these apps do not directly identify the medication or the dose prior to the patient taking the medication, and are not of particular use in conjunction with syringes or pen injectors.

There are smartphone other apps that assist users with recording medical events such as injections, and smart injection devices that can assist users with automatically logging dialed amounts for delivery and/or delivered amounts of medication.

Nonetheless, there remains a continuing need for methods and devices to assist users (e.g., patients, their caregivers, their healthcare providers and other medical condition management stakeholders such as payers/insurance companies, pharmacies, and medical products suppliers and distributors) in the acquisition and use of information related to medical condition management events to prevent medical errors such as medication delivery errors, as well as to improve related processes such as replenishment of medical supplies, tracking compliance with medical condition management protocol or regimen, and information sharing among medical condition management stakeholders for optimal patient treatment plan of care, billing, and insurance coverage purposes.

A typical syringe 100, illustrated in FIG. 1, is made primarily of plastic and has several key components including a barrel 10, a stopper 20, a plunger rod 25, and a needle 30. The scale printing 12 on the barrel 10 is used to enable proper dosing by the user. Inside the barrel 10 is the rubber stopper 20 that is used to create a hermetic seal and displace the liquid medication other fluid into and out of the barrel. The plunger rod 25 interfaces with the rubber stopper 20 to move it back and forth under the user's control. A metal needle 30 or cannula is usually attached to the distal end of the barrel to allow fluids to be injected into or removed from the body, although this is not always the case. For example, a syringe having a male Luer connector at its distal end can be attached to a female Luer connector on a catheter or IV line to inject or withdraw fluids without the use of a needle or cannula.

Large numbers of syringes may be used in a relatively short period of time in hospital and care settings, and for management, by patients, of certain conditions. A needle may be detachably connected to a barrel using Luer-Lok™ or Luer slip connections, or they may be permanently attached or "staked" to the barrels during manufacture of the syringes.

Effective administration of some types of drug injections, particularly in the case of insulin used by diabetics, requires that a record be kept of all administered doses. While education is offered for home injection patients, most patients still find it challenging to follow the instructions properly on a daily basis. Additionally, the only means for obtaining a record of injections and dosages injected is by writing it down manually. Health care personnel can record dose-related information in a clinical setting, but there is significant overhead associated with capturing this information. It is also difficult to measure and record certain injection times and dosages. Certain patients may also find it difficult to draw a very specific amount of a drug into a syringe and/or determine a specific amount of a drug that has been injected due to a difficulty in reading scale markings on the barrel of the syringe or in appropriately following instructions.

A need exists for an improved syringe that can provide a user with more accurate information regarding delivered dose and adherence to a prescribed medication dosage regimen.

SUMMARY

Example embodiments may address at least the above problems and/or disadvantages and other disadvantages not described above. Also, example embodiments are not required to overcome the disadvantages described above, and may not overcome any of the problems described above.

According to an aspect of an example embodiment, a smart syringe system includes a syringe and an external apparatus. The syringe includes a body with a first pattern printed thereon and a plunger with a second pattern printed thereon, such that a relative position of the plunger with respect to the body can be determined based on ab optical comparison of relative positions of the first pattern and the second pattern. The apparatus includes an image capture device and a processor configured to analyze the image capture device and thereby determine a fill level of the syringe.

The first pattern may be a scale printed on a barrel of the body of the syringe.

The second pattern may be a series of triangles extending along a length parallel to a length of the plunder.

The apparatus may also include a memory storing software instructions, and the processor may be configured to execute the software instructions and thereby execute an application configured to cause the processor to display information regarding the fill level of the syringe.

According to an aspect of another example embodiment, a smart syringe system includes a syringe and an apparatus external to the syringe. The syringe includes a sensing means for sensing a dose administered to a patient, and a first communication means for transmitting data regarding the dose. The external apparatus includes a second communication means for receiving the data regarding the dose, and a display for displaying information regarding the dose.

The sensing means may be one of a linear encoder and a rotary encoder.

The sensing means may be a sleeve disposed around a barrel of the syringe, the sleeve including a linear encoder.

The first and second communication means may be a near field communication (NFC) transmitter and an NFC receiver, respectively.

According to an aspect of another example embodiment, a method of a syringe system comprises a syringe transmitting data regarding a dose administered to a patient, to an external device, the external device receiving the data; a processor of the device executing software instructions and thereby analyzing the data; and the external device displaying information regarding the dose.

The syringe may transmit the data and the external device may receive the data via NFC.

The syringe may also obtain the data via one of a linear encoder and a rotary encoder.

BRIEF DESCRIPTION OF THE DRAWINGS

The above and/or other example aspects and advantages will become apparent and more readily appreciated from the following description of example embodiments, taken in conjunction with the accompanying drawings in which.

DETAILED DESCRIPTION

Figure 1:
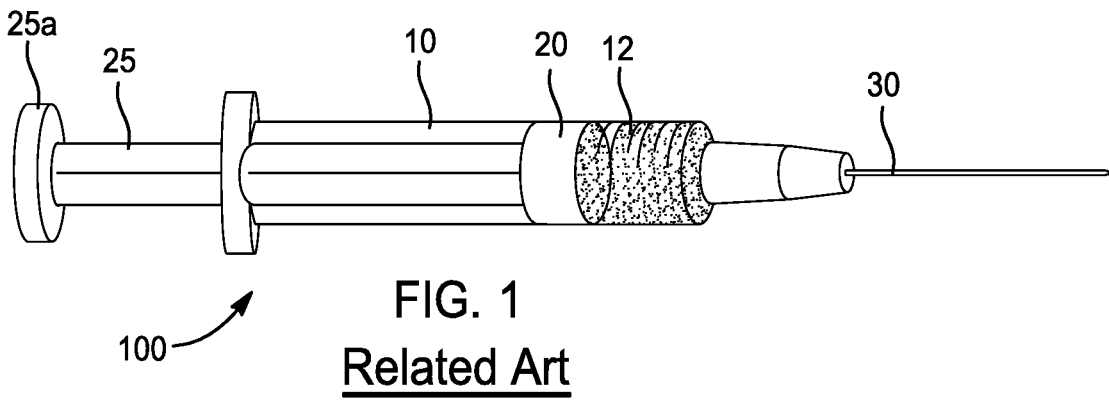
FIG. 1 illustrates a disposable syringe according to the related art.

Reference will now be made in detail to example embodiments which are illustrated in the accompanying drawings, wherein like reference numerals refer to like elements throughout. In this regard, the example embodiments may have different forms and may not be construed as being limited to the descriptions set forth herein.

It will be understood that the terms "include," "including," "comprise," and/or "comprising," when used in this specification, specify the presence of stated features, integers, steps, operations, elements, and/or components, but do not preclude the presence or addition of one or more other features, integers, steps, operations, elements, components, and/or groups thereof.

It will be further understood that, although the terms "first," "second," "third," etc., may be used herein to describe various elements, components, regions, layers and/or sections, these elements, components, regions, layers and/or sections may not be limited by these terms. These terms are only used to distinguish one element, component, region, layer or section from another element, component, region, layer or section.

As used herein, the term "and/or" includes any and all combinations of one or more of the associated listed items. Expressions such as "at least one of," when preceding a list of elements, modify the entire list of elements and do not modify the individual elements of the list. In addition, the terms such as "unit," "-er (-or)," and "module" described in the specification refer to an element for performing at least one function or operation, and may be implemented in hardware, software, or the combination of hardware and software.

Various terms are used to refer to particular system components. Different companies may refer to a component by different names—this document does not intend to distinguish between components that differ in name but not function.

Matters of these example embodiments that are obvious to those of ordinary skill in the technical field to which these example embodiments pertain may not be described here in detail.

As discussed above with respect to FIG. 1, a related art disposable syringe 100 includes a plastic barrel 10, having scale printing 12 thereon, and a needle 30 attached thereto. A rubber stopper 20, disposed within the barrel 10, is attached to a plunger rod 25. Pressure on a distal end 25*a* of the plunger rod 25, puts pressure on a fluid inside the barrel 10, allowing the fluid to be injected into a body.

According to an example embodiment, a smart syringe comprises means for wirelessly communicating with an external device, and means for sensing one or more of an injected dosage and a fill level.

The means for sending may be one or more of capacitive, resistive, inductive, antenna attenuation, color coded, and digitally encoded.

According to one example embodiment, the means for sensing comprises a resistive film dispose outside the barrel of the syringe or on the plunger shaft of the syringe. Wipers may be arranged so that a resistance between the two wipers changes as the plunger is withdrawn, to draw up medication into the syringe, or depressed, to inject medication into a user. An electrical circuit, which may be disposed under finger tabs or on the thumb rest of the syringe, may monitor the resistance between the wipers and may transmit this information to an external device.

According to another example embodiment, the means for sensing comprises a linear encoder, for example, a Hall effect linear encoder.

Figure 2A:
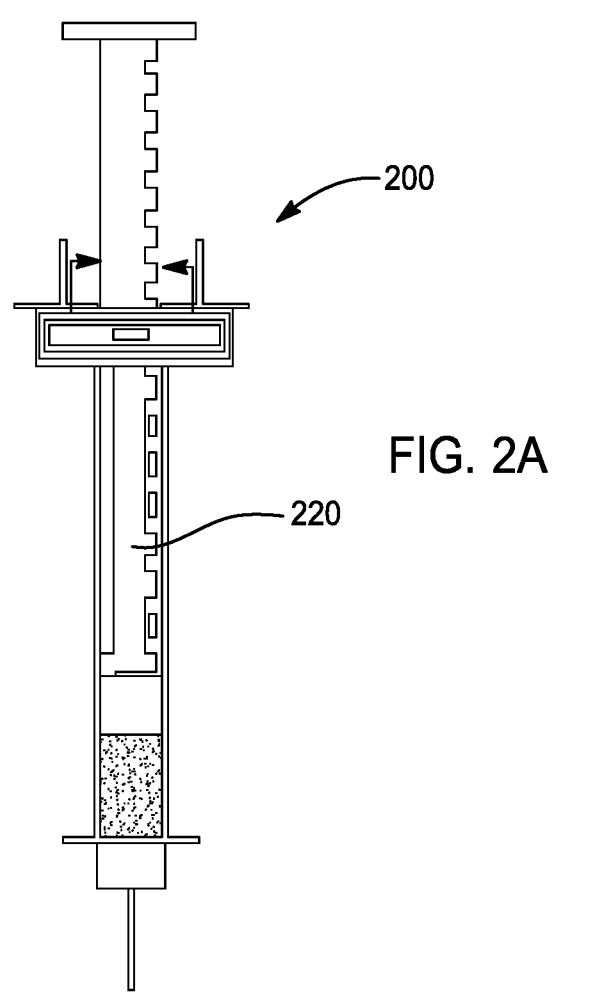
FIGS. 2A, 2B, and 2C illustrate an example smart syringe with a linear encoder, according to an example embodiment.
Figures 2B, 2C:
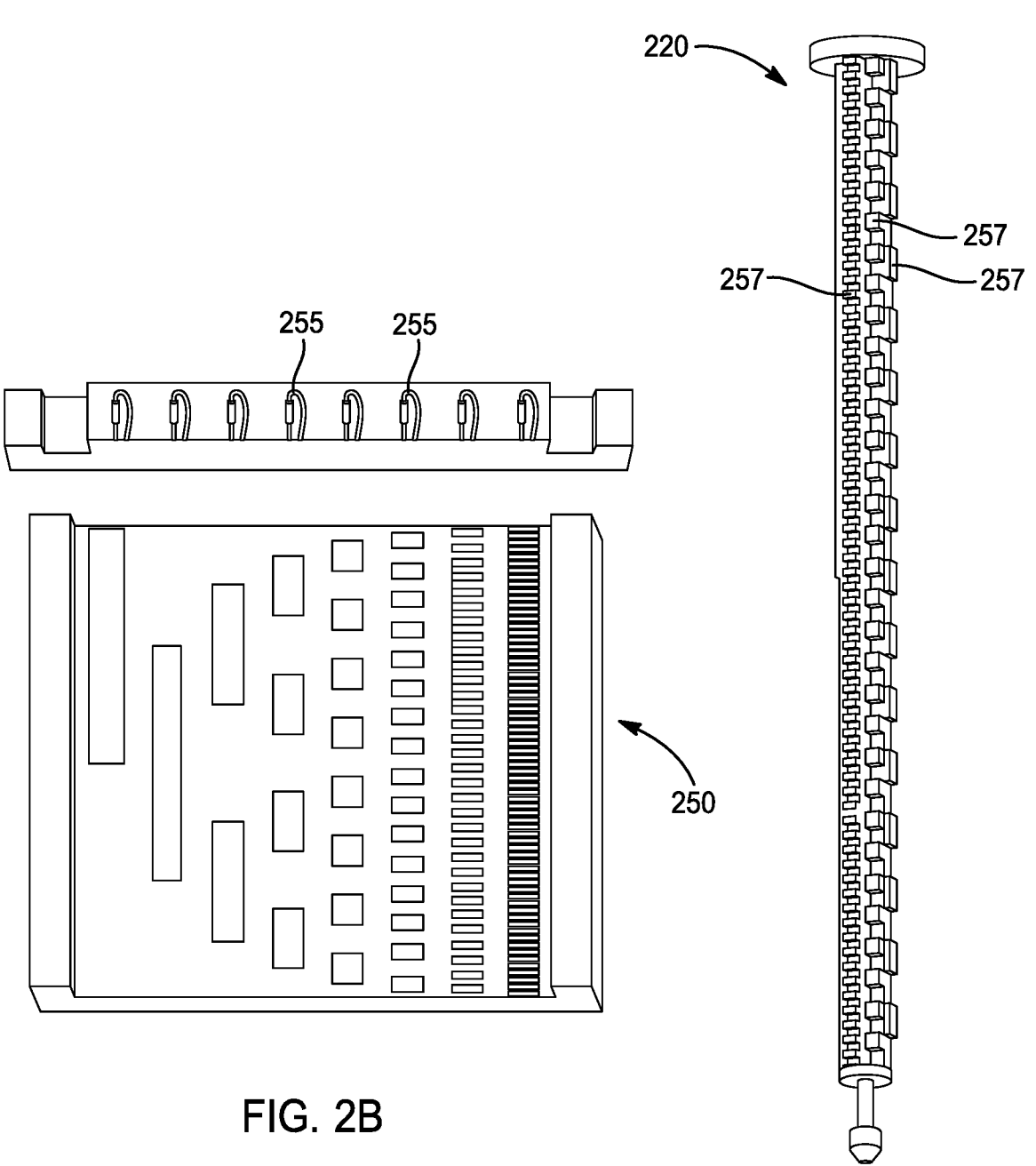

FIGS. 2A, 2B, and 2C illustrate an example smart syringe 200 with a linear encoder 250. The smart syringe 200 includes a digitally-encoded plunger 220 which may be fully disposable. As shown in FIGS. 2B and 2C, the plunger 220 includes a mechanical representation of 1s and 0s that are detectable via switches 255. For example, mechanical switches 255 can detect the humps 257 encoded on the plunger 220, as shown in FIG. 2C. A binary layout or a gray code layout, as shown in FIGS. 2B and 2C, may be used. An 8 bit number detected by the switches 255 may then be transmitted to an external device.

According to another example embodiment, the means for sensing may comprise a sleeve including a linear encoder.

Figures 3A, 3B, 3C:
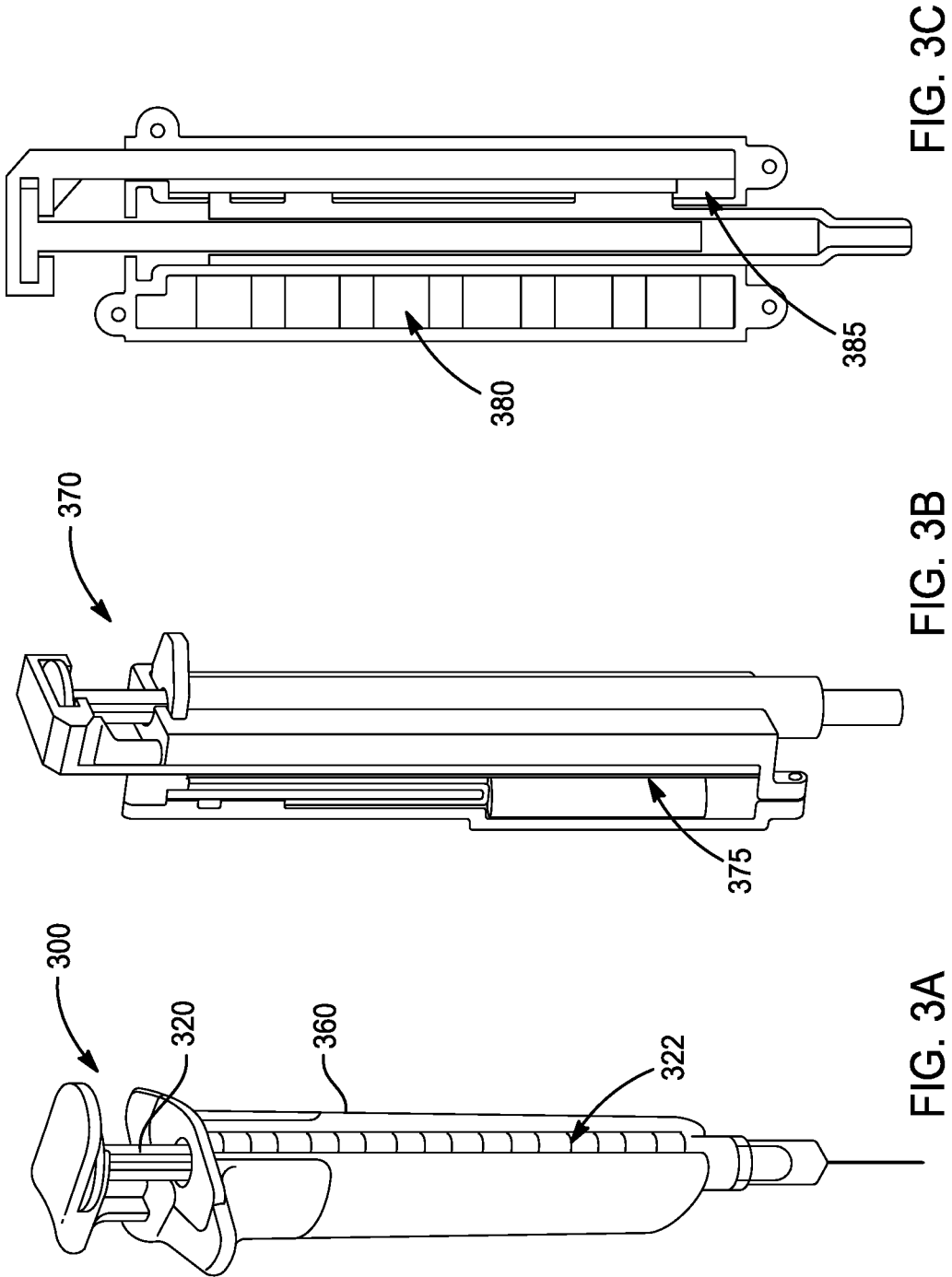
FIGS. 3A, 3B, and 3C illustrate an example smart syringe with a linear-encoding sleeve, according to an example embodiment.

FIGS. 3A, 3B, and 3C illustrate a smart syringe 300 with a reusable sleeve 360 including a linear encoder. The syringe 300, as shown, includes the reusable sleeve 360 including electronics and communication circuitry to determine and relay dose information. The sleeve 360 includes a custom linear encoder that tracks a position of the plunger 320 throughout an injection. As shown in FIG. 3A, when the syringe 300 is initially positioned in the sleeve 360, the gradations 322 on the syringe 300 may be visible. The sleeve 360 may then be closed around the syringe 300. The sleeve may include a hall effect linear encoder 370 and a strip magnet 375, as shown in FIG. 3B. Alternately, the sleeve may include multiple Anisotropic Magneto-Resistive (AMR) sensors 380 with a single magnet 385 disposed on the plunger 320, as shown in FIG. 3C.

Figures 4A, 4B, 4C:
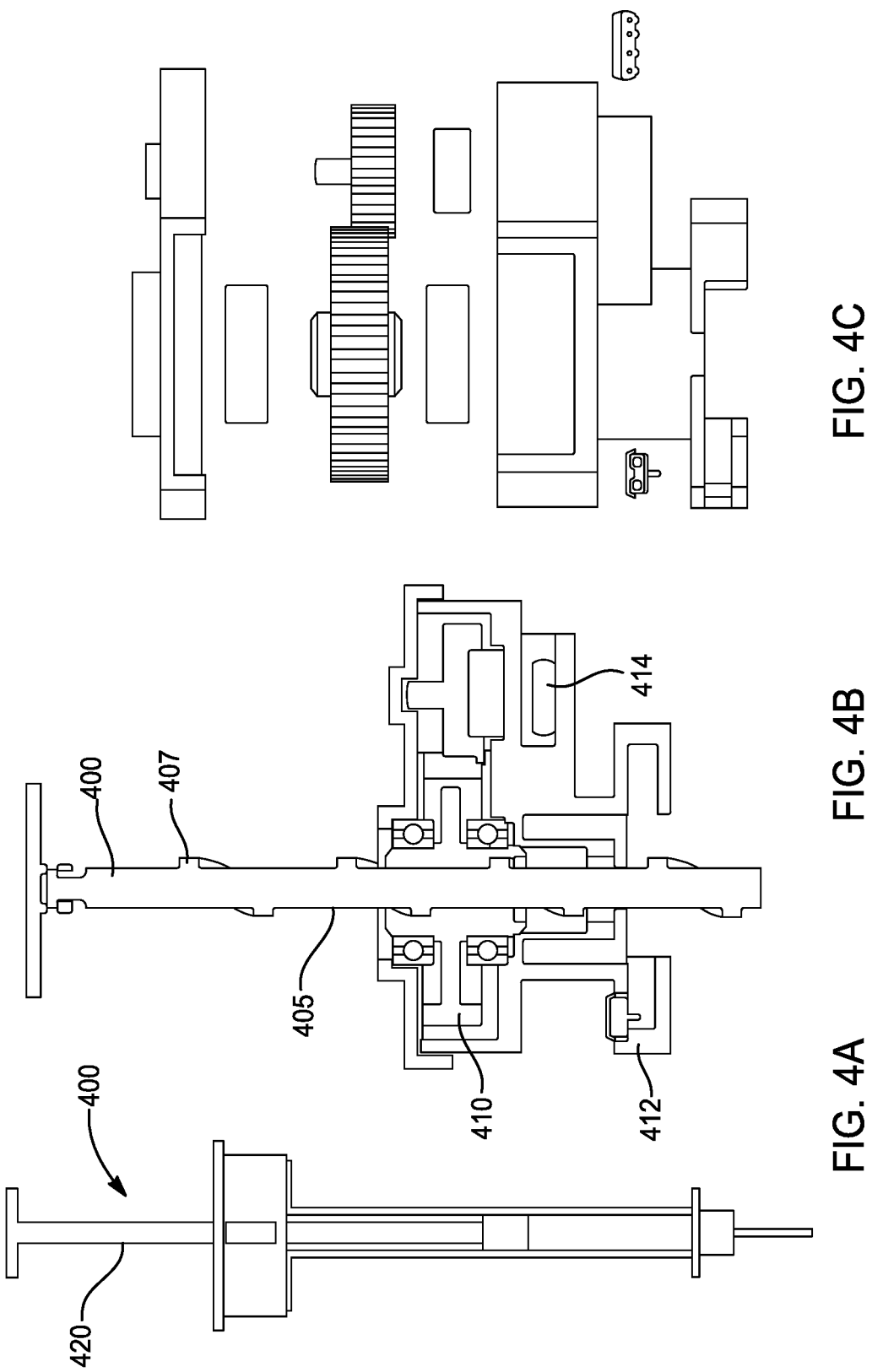
FIGS. 4A, 4B, and 4C illustrate an example smart syringe with a rotary encoder, according to an example embodiment.

According to another example embodiment, the means for sensing may comprise a rotary encoder, FIGS. 4A, 4B, and 4C illustrate a smart syringe including a plunger with a rotary encoder according to an example embodiment. The syringe 400 includes a plunger 420 including a threaded linear portion 405 and a linear-rotary converter 410. The plunger 420 may include square threading 407, as shown in FIG. 4B, the linear movement of which is converted into rotary motion by the converter 410. The converter 410 may also include a switch 412 to detect the presence of the syringe 400, and a diametrically separated magnet with a rotary encoder 414 to detect the rotational movement.

Figures 5A, 5B:
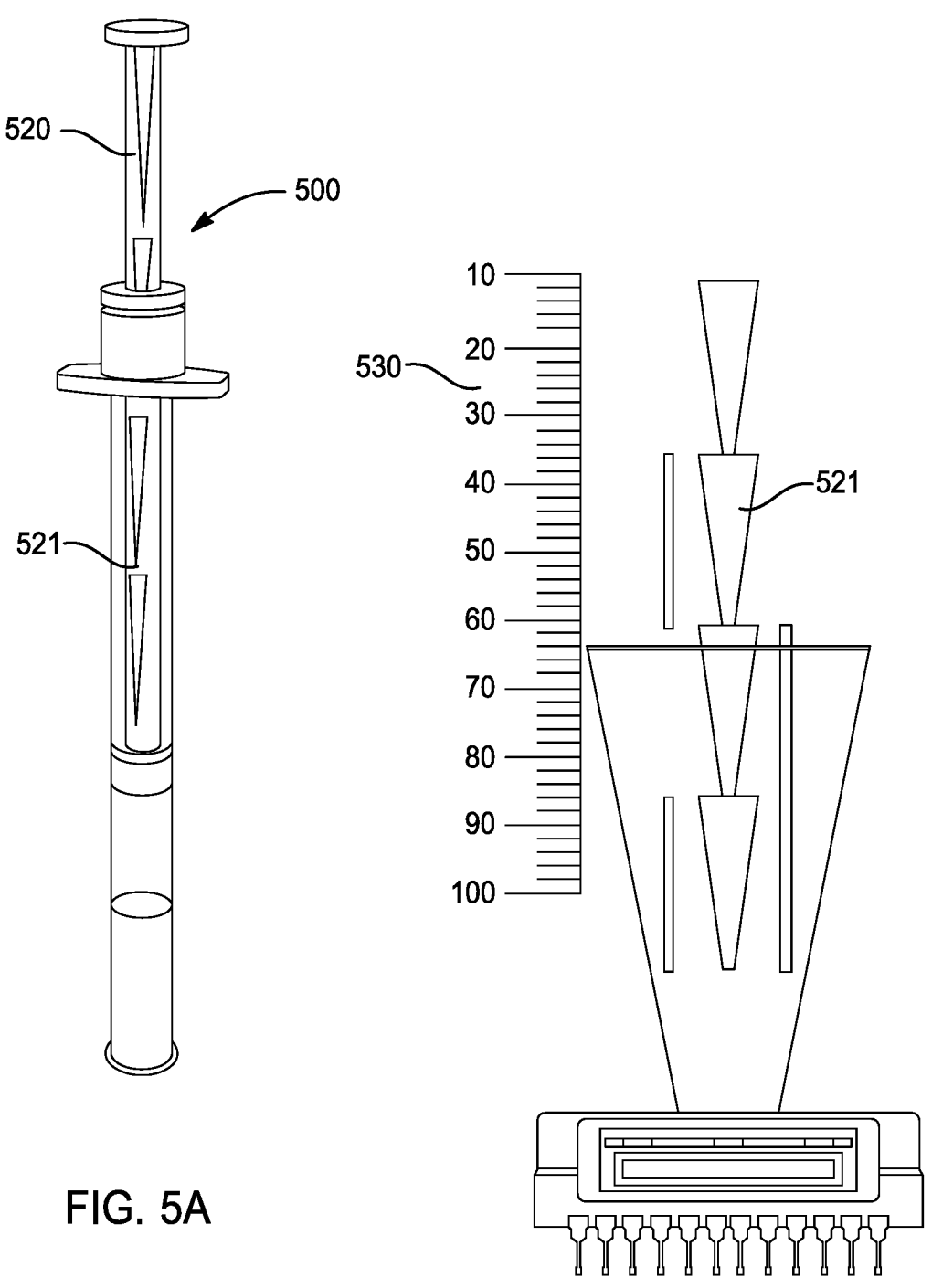
FIGS. 5A and 5B illustrate an example smart syringe with a plunger with a pattern provided thereon, according to an example embodiment.

According to another example embodiment, the means for sensing may comprise an image which can be analyzed and thereby used to determine an injected dosage or a fill level. FIGS. 5A and 5B illustrate a smart syringe 500 including a plunger 520 with a pattern 521 provided thereon that can be read by a smart accessory. As shown in FIG. Bb, the pattern 521 on the plunger 520 aligns with units on the barrel 530 of the syringe 500, such that the smart accessory can read the pattern and derive the units of insulin in the syringe 500. The pattern may comprise a series of triangles, as shown, or other shapes, as would be understood by one of skill in the art. The smart accessory or other external device, which may be an external device such as a mobile phone operating an app as discussed herein, includes an image capture device such as a camera which can obtain an image of the smart syringe. The device also comprises a processor operating the app or other software, thus configuring the device to analyze the image and thereby determine a fill level of the syringe.

Figure 6:
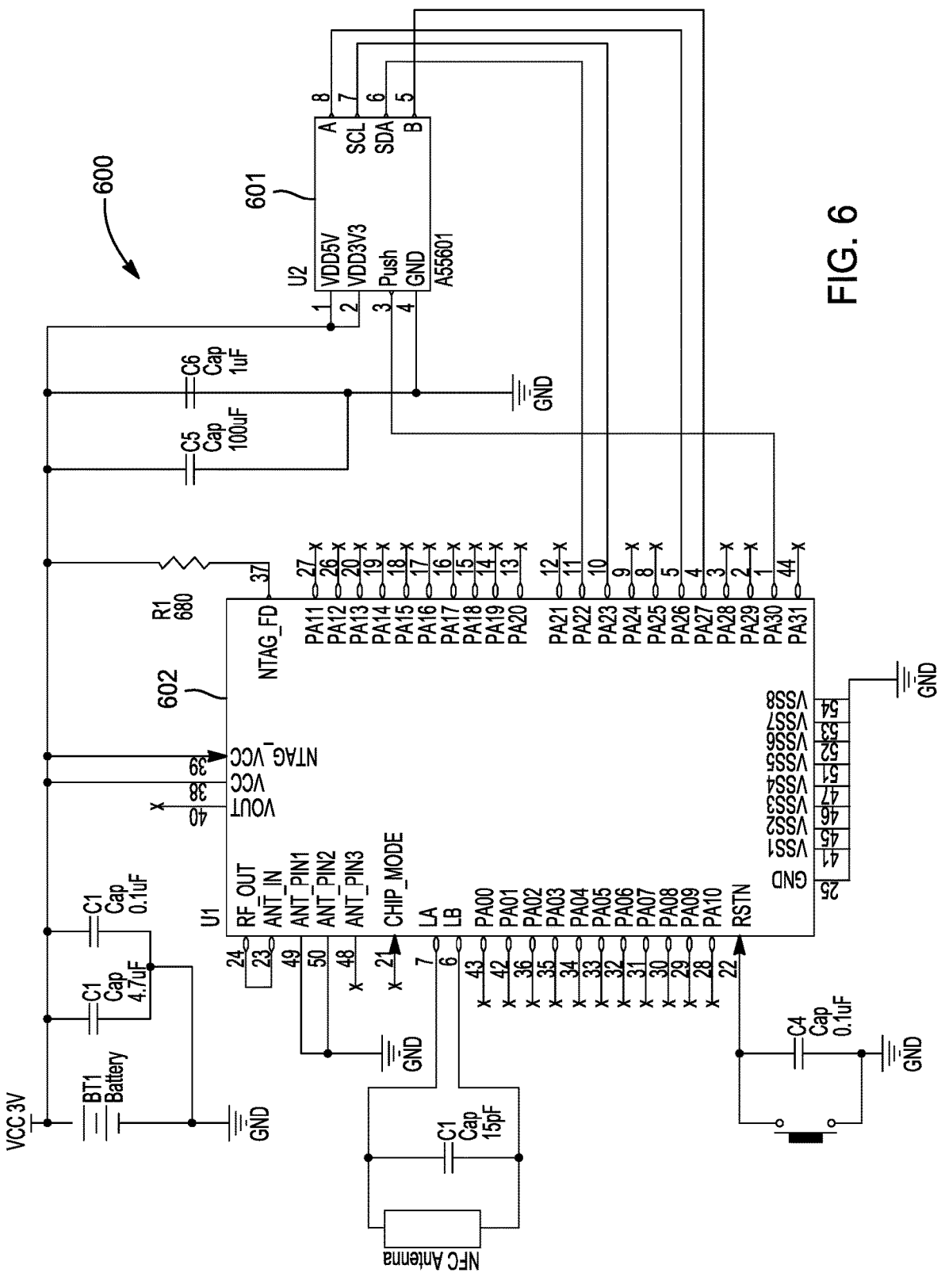
FIG. 6 illustrates circuitry of a rotary encoder, according to an example embodiment.

FIG. 6 illustrates circuitry of a rotary encoder according to an example embodiment. As shown, the rotary encoder 600 includes a magnetic rotary encoder integrated circuit 601 and a microcontroller 602.

According to another example embodiment, the means for sensing may comprise micro-electro-mechanical systems (MEMS) flow sensors.

An accelerometer (not shown) may be included on in any one or more of the example smart syringes described above, in order to determine when the skin is pierced by the needle, enabling a determination of a position of the plunder at a time of injection.

According to example embodiments, the means for communication may be one or more of near field communication (NFC), Bluetooth, Zigbe, and any other system of wireless communication, as would be understood by one of skill in the art.

Figure 7:
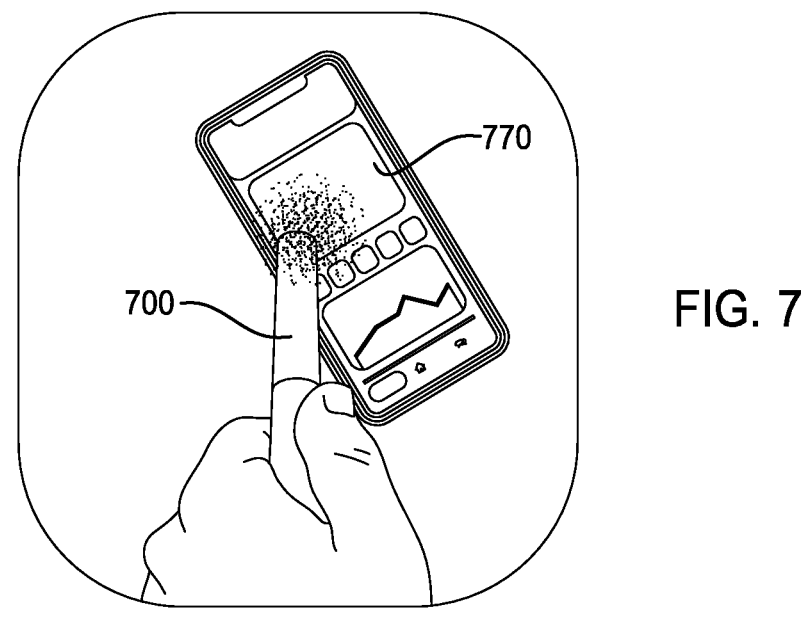
FIG. 7 illustrates a smart syringe tapping an external device, according to an example embodiment.

According to an example embodiment, a smart syringe 700 including an NFC chip can be placed into close proximity with ("tapped") a smart device 770 such as a phone including an app, as shown in FIG. 7.

Figure 8:
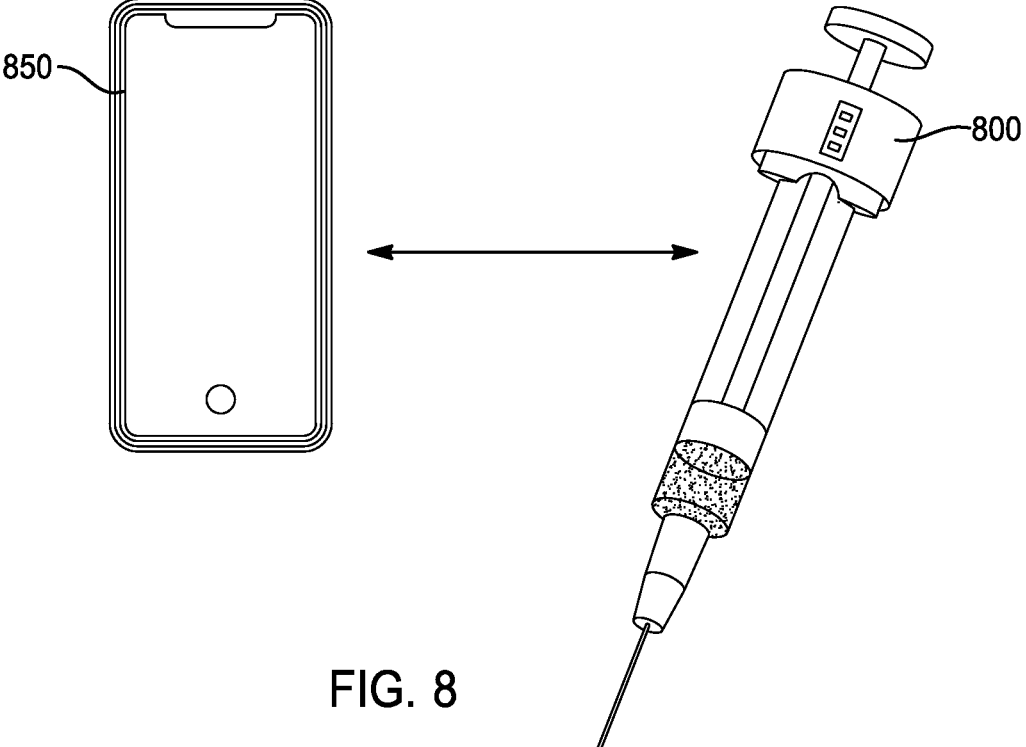
FIG. 8 illustrates a system including a smart syringe and an external device, according to an example embodiment.

FIG. 8 illustrates a smart syringe system including a smart syringe 800 and an external device 850 enabled with an app. In FIG. 8, the smart syringe 800 is illustrated as a smart syringe including a plunger with a rotary encoder. However, the smart syringe 800 may be any smart syringe as discussed with respect to the above embodiments. The external device 850 may be, for example, a smart phone, as illustrated, or a laptop, tablet, personal computer, or other processing device enabled with an app. The smart syringe 800 and the external device 850 enabled with the app may be connected wirelessly, by NFC, for example. The two communicating platforms may have different combinations of hardware and software. Data transfer between the devices may differ depending on when and how data transfer occurs between the smart syringe 800 and the external device 850. For example, the smart syringe 800 may transfer data regarding drug delivery status (e.g. complete or incomplete) or other delivery informatics (e.g. rate, timing, etc.) in real time (i.e. during injection) or at any time after injection, such as when previously disconnected devices are eventually paired or otherwise connected. The communication connectivity may be conducted via any type of wireless connectivity methods including, but not limited to NFC, Bluetooth™, and WiFi, which may impact device pairing, if needed, and a need for proximity of the devices. The appropriate proximity of the devices relative to each other depends on the connectivity method used, as would be understood by one of skill in the art. The timing of data transfer may depend at least in part on whether or not the two communicating platforms and or at least the smart syringe 800 has a time recording capability.

In accordance with an aspect of an example embodiment, the external device 850 may be a smart phone provided with a delivery informatics app to connect to and cooperate with the smart syringe 800. A user may pair the smart phone with the smart app for synchronization using, for example, standard NFC technology methods.

Data synchronization between the smart syringe 800 and the app can occur with every injection, for example, to obtain delivery data. The app may advantageously provide time recording capability (e.g., data provided during or immediately after an injection may be stored in the external device 850 or in an external memory, e.g. the cloud, with a time stamp).

Regarding the app described herein, it may be a standalone app stored and operating on a smartphone or other external device 850, as discussed above, or may be provided as an enhancement to a digital health app. The medical event image capture app can also be integrated into a digital health app (e.g., the BD® Diabetes Care app). For example, the app and its generated informatics can be automatically combined with other digital health app content, such as logs of injections, exercise, carbohydrates intake and blood glucose readings, to assist the patient and disease management stakeholders in tracking a patient's compliance with a prescribed disease management regime (e.g., how well the patient is maintaining target blood glucose levels), reordering supplies (e.g., home health supplies such as self-injection devices and medication, and pharmacy inventory) and auto-shipping of prescribed medications and medical supplies to patients or commercial settings, inventory tracking, billing for medical events captured within clinical settings, and the like. Alternately, the app can be a standalone app that communicates with the user (e.g., patient) or other stakeholders on the patient's medical condition management team such as caregivers (e.g., parents, spouses, school nurses), health care providers, clinical setting administrators, pharmacies, payers (e.g., insurance companies), and medical device suppliers and distributors.

Example embodiments described herein are with reference to diabetes management and injection of insulin. However, is to be understood that the operations of the app as described herein can be used for reducing errors with respect to management or treatment of other medical conditions that require use of various devices and medical condition management procedures such as surgical instruments, blood collection and delivery products, delivery of other medications besides insulin, and so on. For example, the example embodiments can be used to reduce medical errors associated with self-injection using other types of medications, correct use of surgical tools for a selected medical procedure, correct use of equipment for IV delivery of medical fluids to patients, and the like.

FIGS. 9A through 9E illustrate example information which an app may cause to display on a smartphone.

Figure 9A:
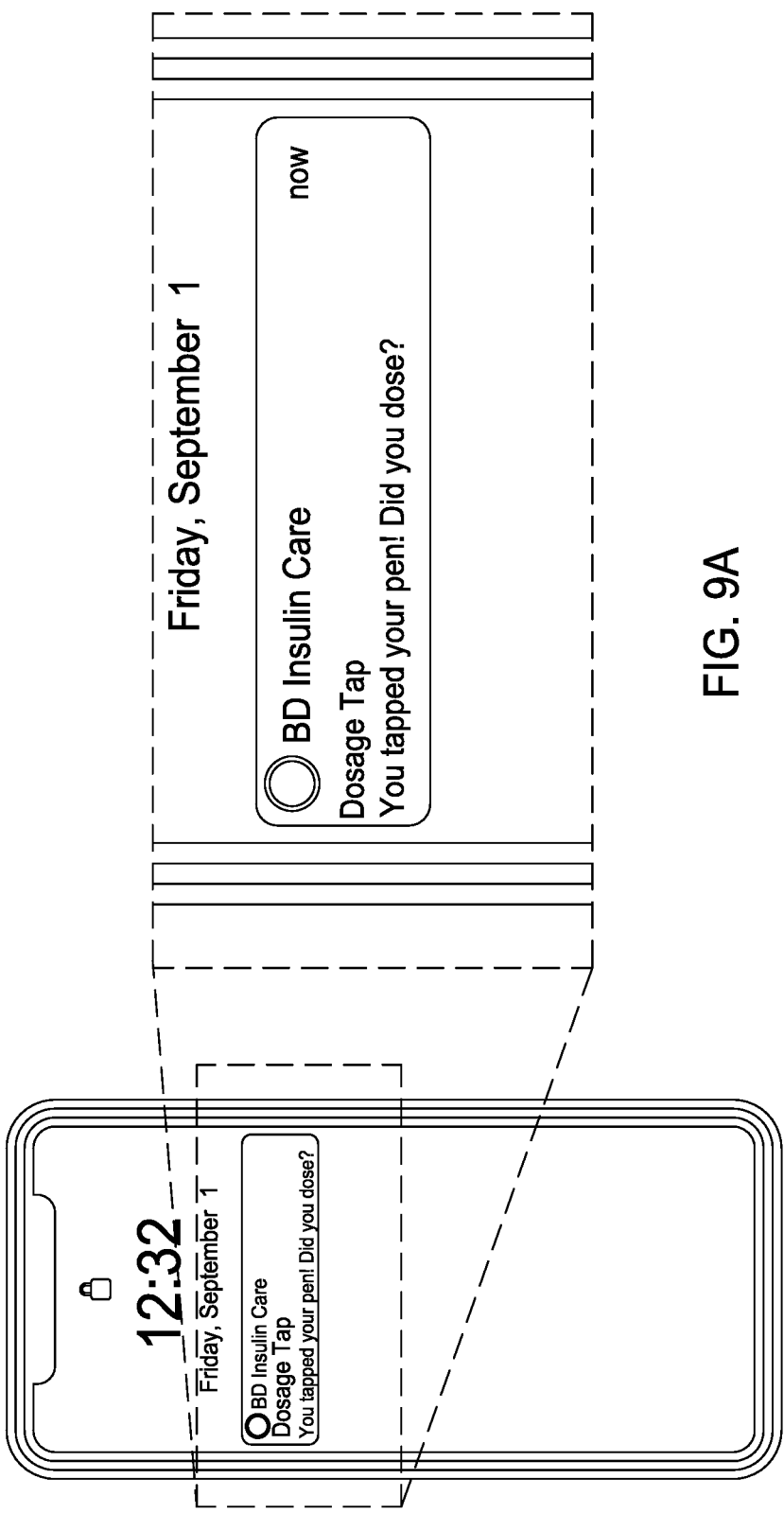
FIGS. 9A through 9E illustrate information which an app may cause to display on an external device, according to an example embodiment.
Figure 9C:
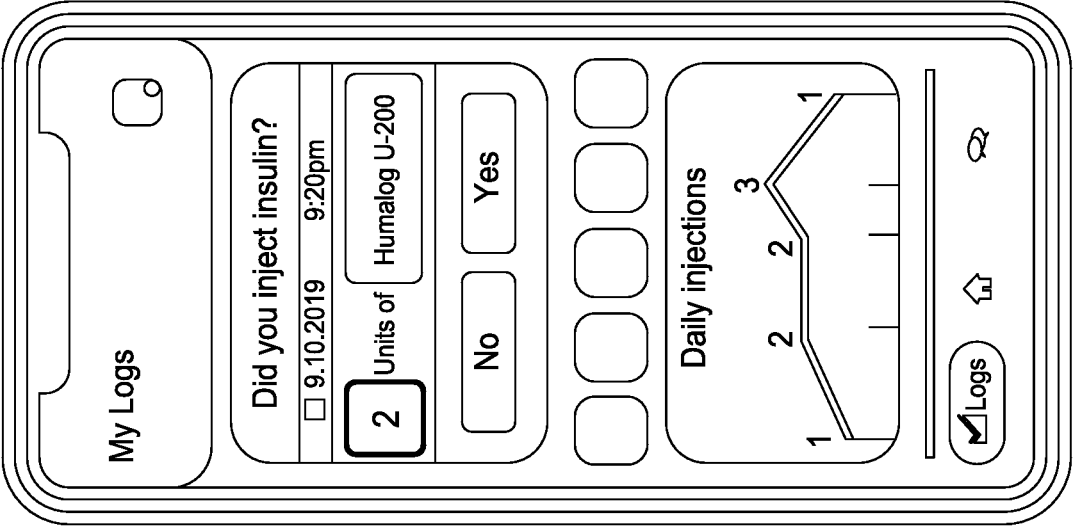
Figure 9B:
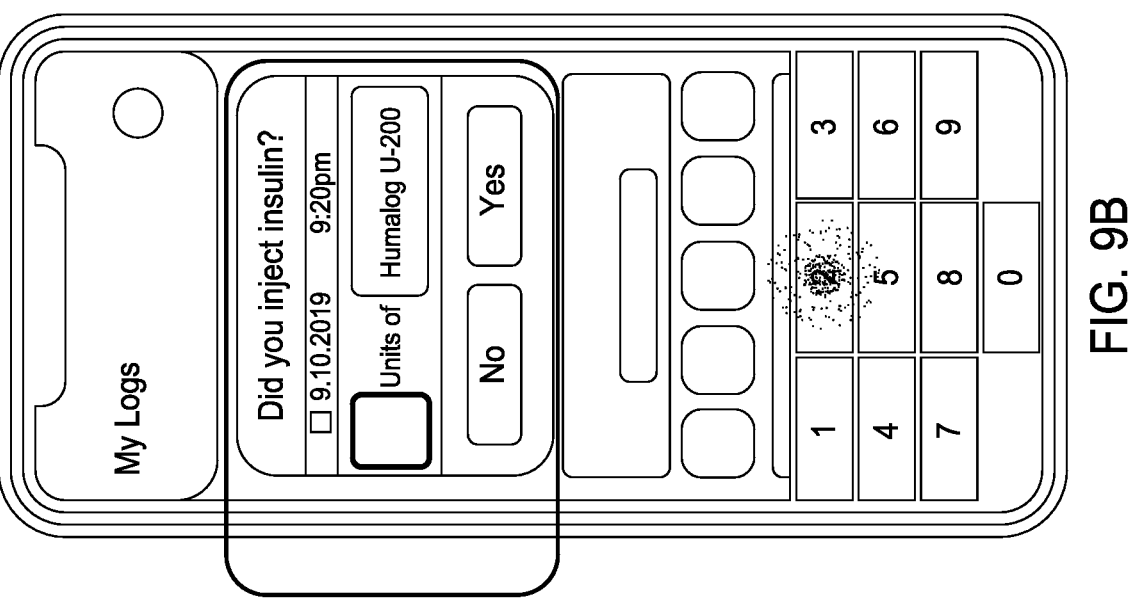
Figure 9E:
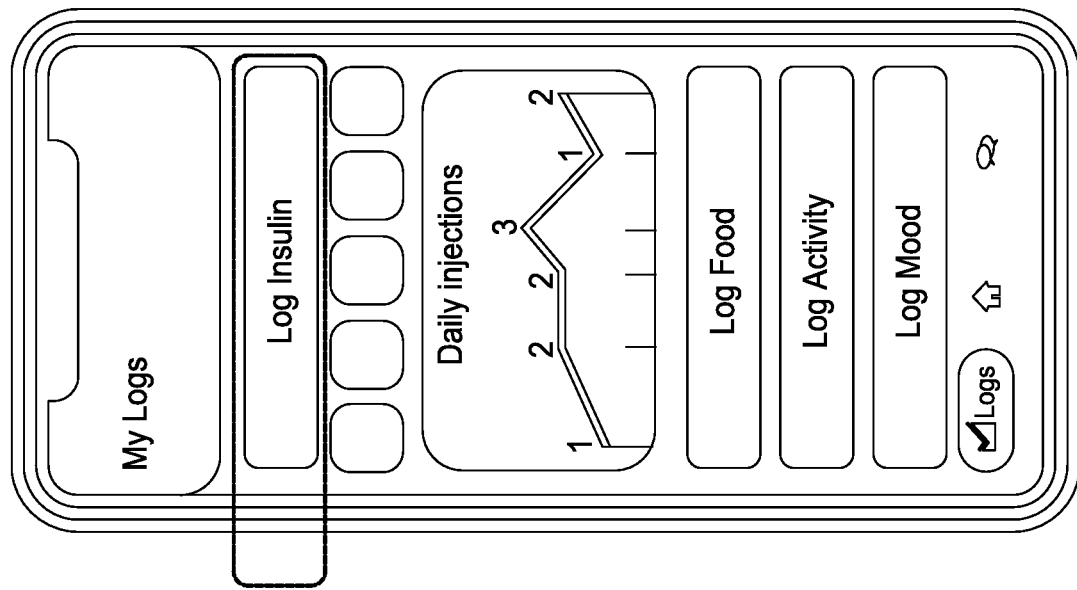
Figure 9D:
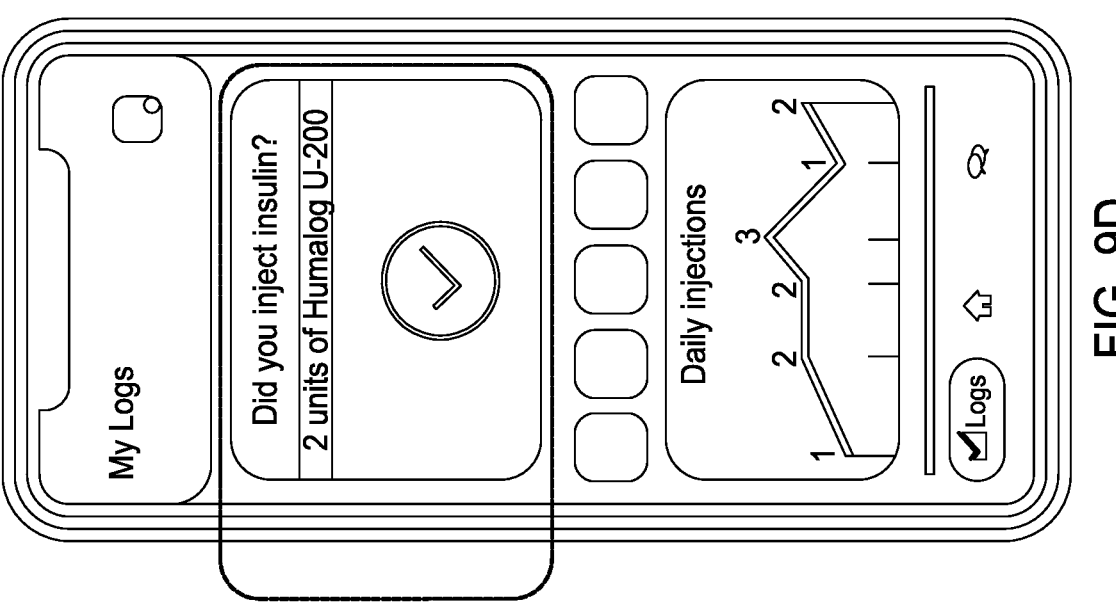

Tapping (i.e. bringing into close proximity) the smart syringe, including the NFC transmission capabilities, on the external device running the app may cause the app to display or otherwise output a notification to the user, as shown in FIG. 9A. FIG. 9B illustrates an example display screen of the app when opened, prompting a user to enter units of dosage, FIG. 9C illustrates an example display screen of the app when a dosage has been entered, requesting confirmation of the type of insulin injected. FIG. 9D illustrates an example display screen when an injection has been confirmed. FIG. 9E illustrates an example display screen enabling a user to manually log an insulin dose by tapping a button. Other optional logs are displayed below the insulin log.

The components of the illustrative devices, systems and methods employed in accordance with the illustrated embodiments described herein can be implemented, at least in part, in digital electronic circuitry, analog electronic circuitry, or in computer hardware, firmware, software, or a combination thereof. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or other device or on multiple device at one site or distributed across multiple sites and interconnected by a communication network. Also, functional programs, codes, and code segments for accomplishing features described herein can be easily developed by programmers skilled in the art. Method steps associated with the example embodiments can be performed by one or more programmable processors executing a computer program, code or instructions to perform functions (e.g., by operating on input data and/or generating an output). Method steps can also be performed by, and apparatuses described herein can be implemented as, special purpose logic circuitry, e.g., a field programmable gate array (FPGA) or an application-specific integrated circuit (ASIC), for example.

The various illustrative logical blocks, modules, and circuits described in connection with the embodiments described herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory (ROM) (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Computer-readable non-transitory media includes all types of computer readable media, including magnetic storage media, optical storage media, flash media and solid state storage media. It should be understood that software can be installed in and sold with a central processing unit (CPU) device. Alternately, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

Figure 10:
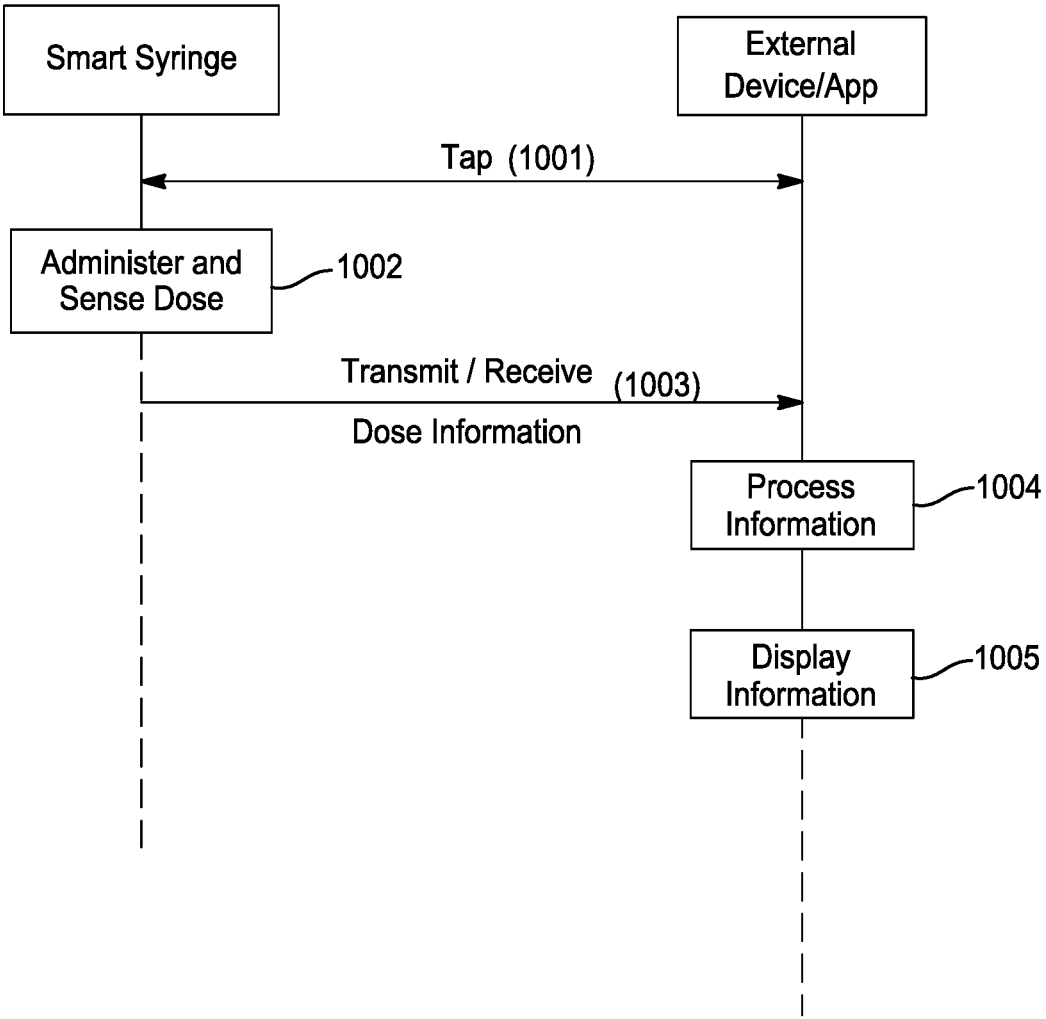
FIG. 10 is a flow chart of operations of a smart syringe and external device, according to an example embodiment.

FIG. 10 is a flow chart of operations of a smart syringe and external device according to an example embodiment. As shown the smart syringe "taps" the external device, establishing communication therebetween (1001). As shown in FIG. 10, the tapping occurs prior to administration of a dose. However, alternately, the tapping may occur at a later point in time, after administration of the dose. The smart syringe administers the dose to the patient and senses the dosage (1002). Information regarding the dose is transmitted to the app as operated on the external device (1003). The app then processes the received information (1004) and displays information to the patient (1005).

It may be understood that the example embodiments described herein may be considered in a descriptive sense only and not for purposes of limitation. Descriptions of features or aspects within each example embodiment may be considered as available for other similar features or aspects in other example embodiments.

While exemplary embodiments have been described with reference to the figures, it will be understood by those of ordinary skill in the art that various changes in form and details may be made therein without departing from the spirit and scope as defined by the following claims.

What is claimed is:

1. A smart syringe system comprising:

a syringe comprising:

a body having a scale formed thereon, and a plunger having a series of triangles formed thereon extending along a length parallel to a longitudinal axis of the plunger, such that a relative position of the plunger with respect to the body can be determined based on an optical comparison of relative positions of the scale and the series of triangle; and an apparatus external to the syringe, the apparatus comprising:

an image capture device, and a processor configured to analyze the image capture device and thereby determine a fill level of the syringe.

2. The smart syringe system according to claim 1, wherein the scale is printed on a barrel of the body of the syringe.

3. The smart syringe system according to claim 1, wherein each triangle of the series of triangles is arranged with a base oriented toward a first end of the plunger and a point oriented toward a second end of the plunger.

4. The smart syringe system according to claim 1, wherein the apparatus external to the syringe further comprises a memory storing software instructions, and wherein the processor is configured to execute the software instructions and thereby execute an application configured to cause the processor to display information regarding the fill level of the syringe.

5. The smart syringe system according to claim 1, wherein the apparatus external to the syringe is a mobile phone.

6. A smart syringe system comprising:

a syringe comprising:

sensing means for sensing a dose administered to a patient, the sensing means comprising:

a threading on a plunger of the syringe, and a linear-rotary converter configured to convert a movement of the threading in a linear direction of the longitudinal axis of the plunger into a rotary motion;

first communication means for transmitting data regarding the dose; and an apparatus external to the syringe, the apparatus comprising second communication means for receiving the data regarding the dose, and a display for displaying information regarding the dose.

7. The smart syringe according to claim 6, wherein:

the first communication means comprises at least one of a near field communication (NFC) transmitter and a Bluetooth transmitter, and the second communication means comprises at least one of an NFC receiver and a Bluetooth receiver.

8. The smart syringe according to claim 6, wherein the linear-rotary converter comprises a switch configured to detect a presence of the syringe and a magnet comprising a rotary encoder configured to detect a rotational movement.

9. A method of a syringe system, the method comprising:

a linear-rotary converter of a syringe sensing a movement of threading on a plunger of the syringe, the movement in a linear direction of a longitudinal axis of the plunger;

the linear-rotary converter converting the movement into a rotary motion;

the syringe obtaining data regarding a dose administered to a patient based on the rotary motion;

the syringe transmitting the data to an external device;

the external device receiving the data;

a processor of the external device executing software instructions and thereby analyzing the data; and the external device displaying information regarding to the dose.

10. The method according to claim 9, wherein the syringe transmitting the data comprises transmitting the data via one or more of near field communication (NFC) and Bluetooth, and the external device receiving the data comprises receiving the data via at least one of NFC and Bluetooth.

* * * * *